US012612404B2

(12) United States Patent
Lee et al.

(10) Patent No.: US 12,612,404 B2
(45) Date of Patent: Apr. 28, 2026

(54) IONIC COMPOUND, ABSORBENT AND ABSORPTION DEVICE

(71) Applicant: Industrial Technology Research Institute, Hsinchu (TW)

(72) Inventors: Wei-Chih Lee, Kaohsiung City (TW); Yi-Hsiang Chen, Hsinchu City (TW); Chih-Hao Chen, Hsinchu City (TW); Ai-Yu Liou, Keelung City (TW); Jyi-Ching Perng, Hsinchu County (TW); Jiun-Jen Chen, New Taipei City (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 453 days.

(21) Appl. No.: 18/332,458

(22) Filed: Jun. 9, 2023

(65) Prior Publication Data

US 2024/0132496 A1 Apr. 25, 2024

Related U.S. Application Data

(60) Provisional application No. 63/410,367, filed on Sep. 27, 2022.

(30) Foreign Application Priority Data

Dec. 15, 2022 (TW) ................................. 111148282

(51) Int. Cl.

| | |
|---|---|
| ***C07D 487/08*** | (2006.01) |
| ***B01J 20/22*** | (2006.01) |
| ***C07C 305/04*** | (2006.01) |
| ***C07D 471/08*** | (2006.01) |
| ***C07F 9/09*** | (2006.01) |
| ***C07F 9/28*** | (2006.01) |

(52) U.S. Cl.

CPC ............ *C07D 471/08* (2013.01); *B01J 20/22* (2013.01); *C07C 305/04* (2013.01); *C07F 9/095* (2013.01)

(58) Field of Classification Search

CPC ....... C07D 487/08; C07D 451/02; C07F 9/11; C07F 9/28

USPC .......................................................... 544/349

See application file for complete search history.

(56) References Cited

U.S. PATENT DOCUMENTS

| | | | |
|---|---|---|---|
| 3,489,663 | A | 1/1970 | Bayer et al. |
| 4,841,073 | A | 6/1989 | Hassel et al. |
| 6,033,643 | A | 3/2000 | Yuen et al. |
| 7,638,636 | B2 | 12/2009 | Zhou et al. |
| 8,609,572 | B2 | 12/2013 | Earl et al. |
| 9,011,576 | B2 | 4/2015 | Dinnage et al. |
| 9,768,472 | B2 | 9/2017 | Friesen et al. |
| 9,840,473 | B1 | 12/2017 | Wang et al. |
| 11,207,635 | B2 | 12/2021 | Wang et al. |
| 2003/0148162 | A1 | 8/2003 | Narayanan et al. |
| 2009/0235574 | A1 | 9/2009 | Earle et al. |
| 2011/0247494 | A1 | 10/2011 | Dinnage et al. |
| 2017/0092989 | A1 | 3/2017 | Friesen et al. |
| 2017/0284685 | A1 | 10/2017 | Bahar et al. |
| 2022/0099314 | A1 | 3/2022 | Bahar et al. |

FOREIGN PATENT DOCUMENTS

| | | | |
|---|---|---|---|
| CN | 105732507 | A | 7/2016 |
| CN | 106916284 | A | 7/2017 |
| CN | 108017651 | A | 5/2018 |
| CN | 108017651 | B | 11/2019 |
| CN | 114573741 | A | 6/2022 |
| JP | 61-141786 | A | 6/1986 |
| JP | 62-54153 | A | 3/1987 |
| JP | 62-145086 | A | 6/1987 |
| JP | 63-201188 | A | 8/1988 |
| TW | 201627046 | A | 8/2016 |
| TW | 201923288 | A | 6/2019 |

(Continued)

OTHER PUBLICATIONS

Compounds with RN 191223-77-5, entered in STN on Jul. 16, 1997 and RN 73044-59-4 entered in STN on Nov. 16, 1984.*

(Continued)

*Primary Examiner* — Charanjit Aulakh

(74) *Attorney, Agent, or Firm* — Birch, Stewart, Kolasch & Birch, LLP

(57) ABSTRACT

An ionic compound, an absorbent and an absorption device are provided. The ionic compound has a structure represented by Formula (I):

$$AB_n, \quad \text{Formula (I)}$$

wherein A is

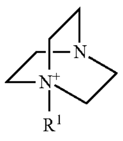
or

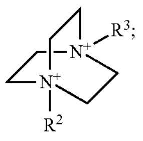

B is

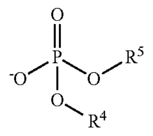
or
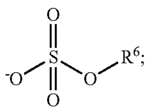

$R^1$, $R^2$, $R^3$, $R^4$, $R^5$, and $R^6$ are independently H, $C_{1-6}$ alkyl group; and n is 1 or 2.

10 Claims, 1 Drawing Sheet

(56) References Cited

FOREIGN PATENT DOCUMENTS

WO WO 2015/145182 A1 10/2015

OTHER PUBLICATIONS

Extended European Search Report for European Application No. 23180602.7, dated Mar. 21, 2024.

Kaman et al., "Dihydrogen Phosphate and Hydrogen Sulphate of 1,4-Dimethyl-1,4-diazabicyclo[2.2.2]octane-1,4-diium: Crystal Structures, Hydrogen Bonding and Infrared Spectra", Journal of Chemical Crystallography, vol. 41, No. 10, Jun. 9, 2011, XP019950950, pp. 1539-1546.

Japanese Office Action for Japanese Application No. 2023-154946, dated Oct. 22, 2024.

Lim et al., "Absorption and desorption of SO2 in aqueous solutions of diamine-based molten salts;" Journal of Hazardous Materials, vol. 289, 2015, pp. 63-71.

Taiwanese Office Action and Search Report for Taiwanese Application No. 111148282, dated Oct. 24, 2023.

Zielinski et al., "Mono N-Alkylated DABCO-Based Ionic Liquids and Their Application as Latent Curing Agents for Epoxy Resins", ACS Applied Polymer Materials, vol. 3, Issue 11, Jul. 7, 2021 (published Oct. 1, 2021), pp. 5481-5493.

Japanese Notice of Allowance for Japanese Application No. 2023-154946, dated Jun. 24, 2025.

Chinese Office Action and Search Report for Chinese Application No. 202310074283.3, dated Dec. 20, 2025.

Cao et al., "Water sorption in ionic liquids: kinetics, mechanisms and hydrophilicity", Phys. Chem. Chem. Phys., 2012, vol. 14, pp. 12252-12262.

Itoh et al., "Dicationic-Type Quaternary Ammonium Salts as Candidates of Desiccants for an Air-Conditioning System", ACS Sustainable Chem. Eng., 2021, vol. 9, pp. 14502-14514.

Ji et al., "Comparative analysis of compression-absorption cascade heat pump using various ionic liquid-based working pairs", Energy Conversion and Management, 2022, vol. 269, pp. 1-16.

Kim et al., "Vapor Pressures of the 1-Butyl-3-methylimidazolium Bromide + Water, 1-Butyl-3-methylimidazolium Tetrafluoroborate + Water, and 1-(2-Hydroxyethyl)-3-methylimidazolium Tetrafluoroborate + Water Systems", J. Chem. Eng. Data, 2004, vol. 49, No. 6, pp. 1550-1553.

Kurnia et al., "Designing ionic liquids for absorptive cooling", Green Chem., 2014, vol. 16, pp. 3741-3745.

Liu et al., "Membrane-based liquid desiccant air dehumidification: A comprehensive review on materials, components, systems and performances", Renewable and Sustainable Energy Reviews, 2019, vol. 110, pp. 444-466.

Luo et al., "A state-of-the-art review on the liquid properties regarding energy and environmental performance in liquid desiccant air-conditioning systems", Applied Energy, 2022, vol. 325, pp. 1-22.

Maekawa et al., "Design of quaternary ammonium type-ionic liquids as desiccants for an air-conditioning system", Green Chemical Engineering, 2020, vol. 1, pp. 109-116.

Mei et al., "A technical review on use of liquid-desiccant dehumidification for air-conditioning application", Renewable and Sustainable Energy Reviews, 2008, vol. 12, pp. 662-689.

Nikfarjam et al., "Antimicrobial Ionic Liquid-Based Materials for Biomedical Applications", Advanced Functional Materials, 2021, pp. 1-27.

Qu et al., "Aqueous solution of [EMIM][OAc]: Property formulations for use in air conditioning equipment design", Applied Thermal Engineering, 2017, vol. 124, pp. 271-278.

Salikandi et al., "Recent trends in liquid desiccant materials and cooling systems: Application, performance and regeneration characteristics", Journal of Building Engineering, 2021, vol. 33, pp. 1-15.

Watanabe et al., "Design of ionic liquids as liquid desiccant for an air conditioning system", Green Energy and Environment, 2019, vol. 4, pp. 139-145.

* cited by examiner

100
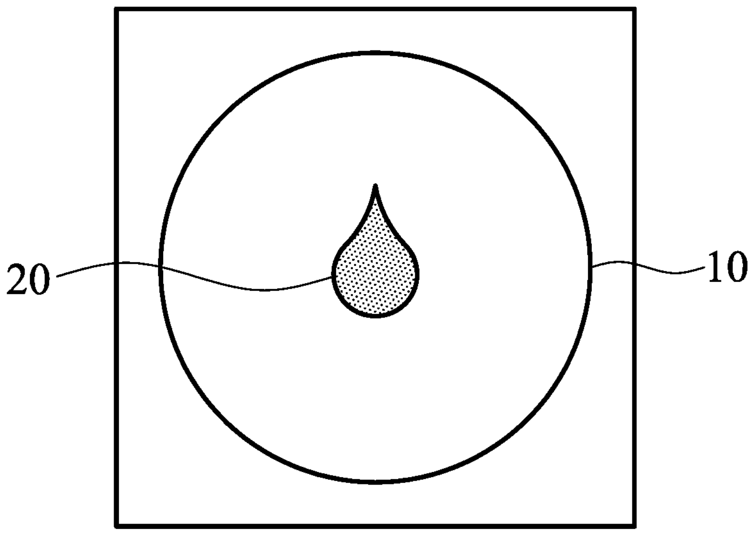

IONIC COMPOUND, ABSORBENT AND ABSORPTION DEVICE

CROSS REFERENCE TO RELATED APPLICATIONS

This application claims priority to U.S. Provisional Application Ser. No. 63/410,367, filed on Sep. 27, 2022, the entirety of which is incorporated by reference herein. Further, the application claims priority of Taiwan Patent Application No. 111148282, filed on Dec. 15, 2022, the entirety of which is incorporated by reference herein.

BACKGROUND OF THE INVENTION

Field of the Invention

The disclosure relates to an ionic compound, absorbent, and absorption device thereof.

Description of the Related Art

Liquid absorbents have several advantages. They have high water-vapor absorption, low regeneration temperature, and low energy consumption. They are easy to transport, and waste heat long-distance utilization. As a result, they are widely used in dehumidification systems. Liquid absorbent dehumidification systems are key equipment for reducing carbon emissions and may aid in raising corporate ESG scores in the future.

Liquid absorbents are liquid materials that can directly absorb water vapor from the air to achieve a dehumidification effect. The driving force is the difference between the water vapor pressure in the air and the saturation vapor pressure of the liquid absorbent surface. Conventional liquid absorbents include aqueous solutions of chlorinated lithium, lithium bromide, lithium chloride, calcium chloride, and magnesium chloride. However, these salt solutions have strong corrosive properties on metals, which can seriously affect the reliability and service life of the dehumidification system. Although titanium can be used as a heat exchanger to avoid corrosion, this significantly increases the cost of building the dehumidification system. In addition, conventional salt solutions tend to crystallize and precipitate when saturated, leading to poor dehumidification performance and serious maintenance issues in the system, such as blockages of the circulation pump.

Both academia and industry have proposed using ionic compounds as liquid absorbents. However, conventional ionic compounds used as liquid absorbents still have corrosive properties on metals, and their water vapor absorption and desorption capabilities still require improvement.

SUMMARY

According to embodiments of the disclosure, the disclosure provides an ionic compound. The ionic compound has a structure represented by Formula (I)

$AB_n$ Formula (I)

wherein, A is

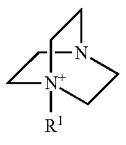

or

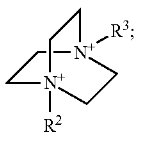

B is

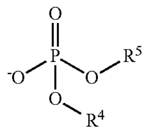

or

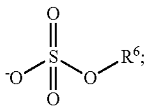

$R^1$, $R^2$, $R^3$, $R^4$, $R^5$, and $R^6$ are independently $C_{1-6}$ alkyl group; and n is 1 or 2.

According to embodiments of the disclosure, the disclosure also provides an absorbent. The absorbent includes the ionic compound of the disclosure.

According to embodiments of the disclosure, the disclosure also provides an absorption device. The absorption device includes a chamber, and the absorbent of the disclosure, wherein the absorbent is disposed in the chamber.

BRIEF DESCRIPTION OF THE DRAWINGS

The present invention can be more fully understood by reading the subsequent detailed description and examples with references made to the accompanying drawings, wherein:

FIGURE is a schematic view of the absorption device according to embodiments of the disclosure.

DETAILED DESCRIPTION OF DISCLOSED EMBODIMENTS

The ionic compound, absorbent, and absorption device of the disclosure are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments. As used herein, the term "about" in quantitative terms refers to plus or minus an amount that is general and reasonable to persons skilled in the art.

The disclosure provides an ionic compound, absorbent, and absorption device employing the same. According to embodiments of the disclosure, the ionic compound consists of a cationic moiety A and an anionic moiety B, wherein the cationic moiety A may be a quaternary ammonium cationic moiety derived from 1,4-diazabicyclo[2.2.2]octane, and the anionic moiety B may be an anionic moiety derived from alkyl phosphate or alkyl sulfate. Due to the combination of the specific cationic moiety A and the specific anionic moiety B, the liquid absorbent employing the ionic compound of the disclosure exhibits higher water-vapor absorption capacity and lower desorption temperature (able to desorb at 60° C. or lower), thereby increasing the dehumidification efficiency of the absorption device that utilizes the absorbent. Moreover, the liquid absorbent employing the ionic compound of the disclosure has various advantages such as odorless, antibacterial, low corrosiveness, fluidity, and excellent room temperature stability, which can be widely applied to various dehumidification devices.

According to embodiments of the disclosure, the disclosure provides an ionic compound. The ionic compound having a structure represented by Formula (I)

$AB_n$ Formula (I)

wherein, A may be

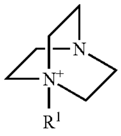 or 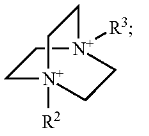

B may be

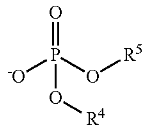 or 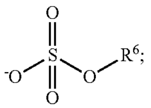

$R^1$, $R^2$, $R^3$, $R^4$, $R^5$, and $R^6$ are independently H, $C_{1-6}$ alkyl group; and n is 1 or 2.

According to embodiments of the disclosure, $C_{1-6}$ alkyl group may be linear or branched alkyl group. For example, $C_{1-6}$ alkyl group of the disclosure may be methyl, ethyl, n-propyl, isopropyl, n-butyl, sec-butyl, iso-butyl, tert-butyl, pentyl or hexyl. Therefore, $R^1$, $R^2$, $R^3$, $R^4$, $R^5$ and $R^6$ may be independently methyl, ethyl, n-propyl, isopropyl, n-butyl, sec-butyl, iso-butyl, tert-butyl, pentyl or hexyl.

According to embodiments of the disclosure, the ionic compound may consists of a cationic moiety A and an anionic moiety B. According to embodiments of the disclosure, the cationic moiety A may be a monovalent quaternary ammonium cationic moiety derived from 1,4-diazabicyclo[2.2.2]octane, such as

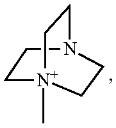, 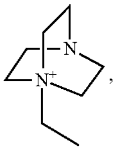, 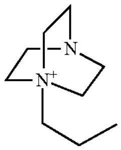, 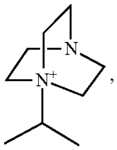, 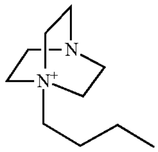, 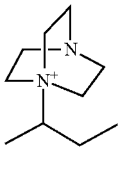, 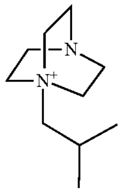, or 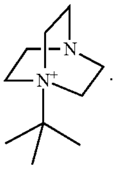.

In addition, According to embodiments of the disclosure, the cationic moiety A may be a divalent quaternary ammonium cationic moiety derived from 1,4-diazabicyclo[2.2.2]octane, such as

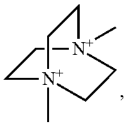, 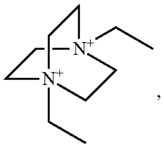, 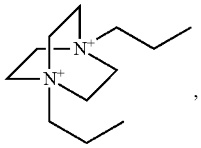, 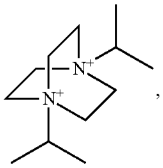, 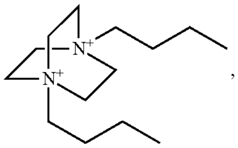, 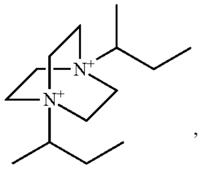, 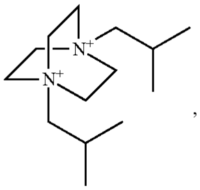, or 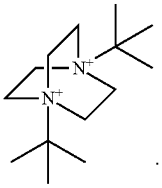.

According to embodiments of the disclosure, the anionic moiety B may be an anionic moiety derived from alkyl phosphate, such as

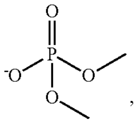, 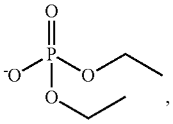, 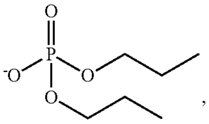, 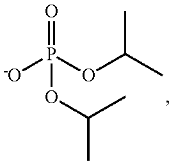, 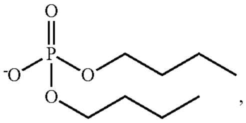, 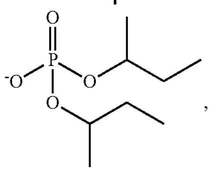, 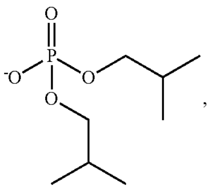, or 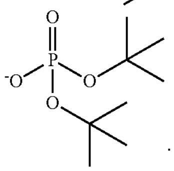.

In addition, according to embodiments of the disclosure, the anionic moiety B may be an anionic moiety derived from alkyl sulfate, such as

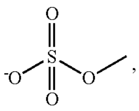,
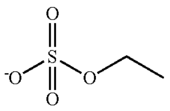,
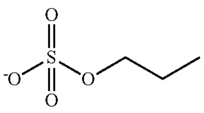,
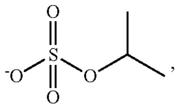,
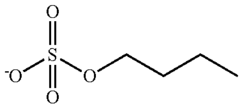,
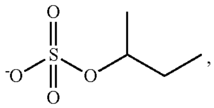,
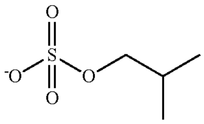, or
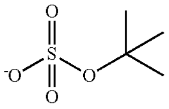.

According to embodiments of the disclosure, the ionic compound having a structure represented by Formula (I)

$AB_n$, Formula (I)

wherein A may be

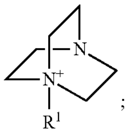;

B may be

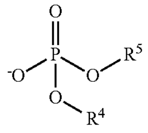 or 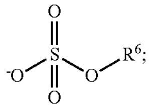;

n may be 1; and $R^1$, $R^4$, $R^5$, and $R^6$ may be independently H, $C_{1-6}$ alkyl group. for example, the ionic compound of the disclosure may be

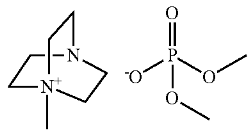,
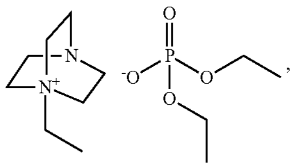,
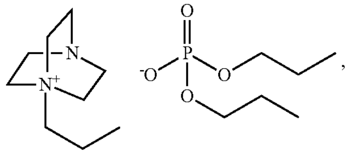,
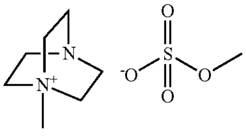,

-continued

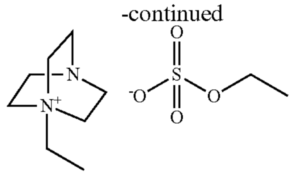, or
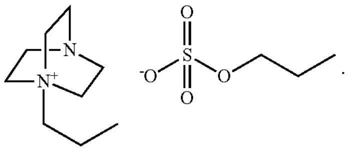.

According to embodiments of the disclosure, the method for preparing the ionic compound having the monovalent quaternary ammonium cationic moiety may include following steps. First, 1,4-diazabicyclo[2.2.2]octane and an anionic precursor is mixed, obtaining a mixture. According to embodiments of the disclosure, the anionic precursor may be alkyl phosphate (such as

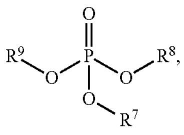, wherein $R^7$, $R^8$, and $R^9$ may be independently H, $C_{1-6}$ alkyl group) or alkyl sulfate (such as

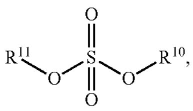, wherein $R^{10}$ and $R^{11}$ may be independently H, $C_{1-6}$ alkyl group). According to embodiments of the disclosure, the molar ratio of 1,4-diazabicyclo[2.2.2]octane to the anionic precursor may be 1:1 to 1:1.2, in order to form an ionic compound having the monovalent quaternary ammonium cationic moiety. Next, the mixture is subjected to a heating process, obtaining the ionic compound of the disclosure. According to embodiments of the disclosure, the heating process may have a temperature of about 50° C. to 150° C., such as 60° C., 70° C., 80° C., 90° C., 100° C., 110° C., 120° C., 130° C., or 140° C. According to embodiments of the disclosure, the heating process may have a time period of 1 hour to 24 hours, such as 2 hours, 4 hours, 6 hours, 8 hours, 10 hours, 12 hours, 16 hours, or 20 hours.

According to embodiments of the disclosure, before subjecting the mixture to a heating process, the mixture and a solvent were mixed, obtaining a solution. According to embodiments of the disclosure, the solvent may be toluene, methanol, ethanol, propanol, butanol, ethyl acetate, anisole, butyl acetate, or a combination thereof. According to embodiments of the disclosure, the solution has a solid content of about 5 wt % to 95 wt %, such as 10 wt %, 20 wt %, 30 wt %, 40 wt %, 50 wt %, 60 wt %, 70 wt %, 80 wt %, or 90 wt %. Herein, the solid content means a weight percentage of the ingredients of the solution except the solvent, based on the total weight of the solution According to embodiments of the disclosure, the ionic compound having a structure represented by Formula (I)

$AB_n$, Formula (I)

wherein A may be

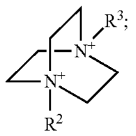

B may be

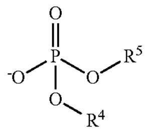 or 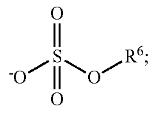

n is 2; and $R^2$, $R^3$, $R^4$, $R^5$, and $R^6$ may be independently H, C1-6 alkyl group. for example, the ionic compound of the disclosure may be

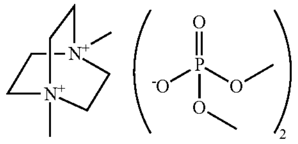

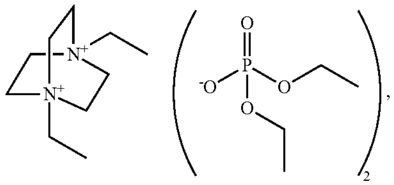

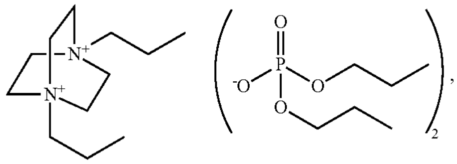

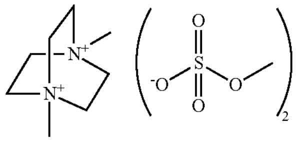

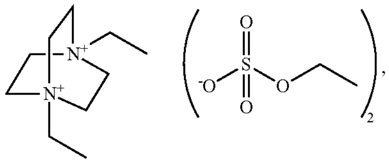 or

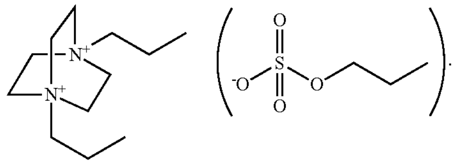

According to embodiments of the disclosure, the method for preparing the ionic compound having the divalent quaternary ammonium cationic moiety may include following steps. First, 1,4-diazabicyclo[2.2.2]octane and an anionic precursor are mixed, obtaining a mixture, wherein the molar ratio of 1,4-diazabicyclo[2.2.2]octane to the anionic precursor is 1:2 to 1:3 (such as 1:2.2, 1:2.3, 1:2.4, 1;2.5, or 1:2.8). According to embodiments of the disclosure. the anionic precursor may be alkyl phosphate (such as

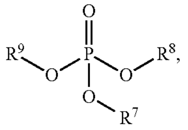

wherein $R^7$, $R^8$, and $R^9$ may be independently H, $C_{1-6}$ alkyl group) or alkyl sulfate (such as

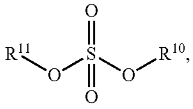

wherein H, $R^{10}$ and $R^{11}$ may be independently $C_{1-6}$ alkyl group). Next, the mixture is subjected to a heating process, obtaining the ionic compound of the disclosure. According to embodiments of the disclosure, the heating process has a temperature of about 50° C. to 150° C., such as 60° C., 70° C., 80° C., 90° C., 100° C., 110° C., 120° C., 130° C., or 140° C. According to embodiments of the disclosure, the heating process has a time period of 1 hour to 24 hours, such as 2 hours, 4 hours, 6 hours, 8 hours, 10 hours, 12 hours, 16 hours, or 20 hours.

According to embodiments of the disclosure, before subjecting the mixture to a heating process, the mixture is mixed with a solvent at first, obtaining a solution. According to embodiments of the disclosure, the solvent may be toluene, methanol, ethanol, propanol, butanol, ethyl acetate, anisole, butyl acetate, or a combination thereof. According to embodiments of the disclosure, the solid content of the solution may be about 5 wt % to 95 wt %, such as 10 wt %, 20 wt %, 30 wt %, 40 wt %, 50 wt %, 60 wt %, 70 wt %, or 80 wt %. Herein, the solid content means a weight percentage of the ingredients of the solution except the solvent, based on the total weight of the solution.

According to embodiments of the disclosure, the disclosure also provides an absorbent. According to embodiments of the disclosure, the absorbent may consist of the ionic compound of the disclosure.

According to embodiments of the disclosure, the absorbent of the disclosure includes the ionic compound of the disclosure and a solvent, in order to uniformly disperse or dissolve the ionic compound of the disclosure in the solvent. According to embodiments of the disclosure, the weight ratio of the ionic compound to the solvent may be about 1:9 to 9:1, such as 2:8, 3:7, 4:6, 5:5, 6:4, 7:3, or 8:2. According to embodiments of the disclosure, the solvent may be water, methanol, ethanol, propanol, butanol, ammonia, or a combination thereof.

According to embodiments of the disclosure, the absorbent of the disclosure includes ionic compound and water, wherein the weight ratio of the ionic compound to the water is 4:1. Herein, the absorbent may have a viscosity of 50 cP to 220 cP at 15° C., such as 60 cP, 80 cP, 100 cP, 120 cP, 150 cP, 180 cP, or 220 cP.

According to embodiments of the disclosure, at the temperature range between 5° C. and 90° C., the state of the absorbent is liquid, i.e. the absorbent has a viscosity in a range of 10 cP to 1,500 cP.

According to embodiments of the disclosure, the absorbent of the disclosure has a relatively large vapor pressure difference at a specific temperature range (such as a range between 15° C. to 50° C. or a range between 15° C. to 60° C.), the absorbent exhibits high dehumidification efficiency and high desorption capability at low temperature.

According to embodiments of the disclosure, the disclosure also provides an absorption device. As shown in FIGURE, the absorption device 100 can include a chamber 10, and the absorbent of the disclosure 20, wherein the absorbent 20 is disposed in the chamber. According to embodiments of the disclosure, the chamber may be a absorb chamber, and the water vapor will be absorbed by the absorbent in the absorb chamber, achieving the purpose of reducing the water vapor content. Due to the extremely low metal corrosiveness of the absorbent of the disclosure, the installation cost of the absorption device could be reduced. Moreover, the absorbent of the disclosure is fluid at a temperature range of 5° C. to 90° C., which makes it suitable for applications in absorption devices that adopt spray or liquid flow processes.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLE

Preparation of Ionic Compound (1)

Example 1

Trimethyl phosphate (0.20 mol) and 1,4-diazabicyclo [2.2.2]octane (0.20 mol) were added into a reaction bottle, and toluene (60 mL) (serving as solvent) was added into the reaction bottle. After heating at 100° C. for 12 hours, the reaction bottle was cooled to room temperature, and the obtained solid was collected. Next, the obtained solid was dissolved in water (50 mL), and water and toluene was removed with a rotary concentrator. Next, the result was subjected to a freeze drying process, obtaining Ionic compound (1) (with a structure of

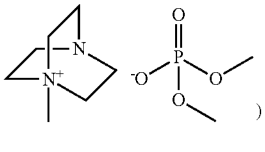

(white solid, with a yield of 98%). The synthesis pathway of the above reaction was as follows:

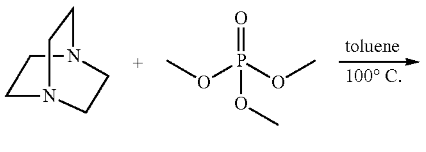

-continued

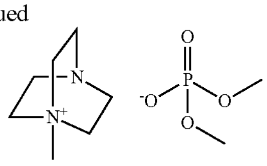

Ionic compound (1)

The measurement results of nuclear magnetic resonance spectrometry of Ionic compound (1) are shown below: $^1H$ NMR (400 MHz, ppm, $CD_3OD$): δ 3.50 (d, J=8.4 Hz, 6H), 3.354 (t, J=6.0 Hz, 6H), 3.20 (t, J=6.0 Hz, 6H), 3.04 (s, 3H).

Example 2

Trimethyl phosphate (0.84 mol) and 1,4-diazabicyclo [2.2.2]octane (0.8 mol) were added into a reaction bottle, and 1-butanol (n-BuOH) (50 mL) (serving as solvent) was added into the reaction bottle. After heating at 60° C. for 12 hours, the reaction bottle was cooled to room temperature. Next, 1-butanol was removed with a rotary concentrator. Next, after baking the result was disposed in a vacuum oven at 110° C. for 12 hours, obtaining Ionic compound (1) (white solid, with a yield of 98%). The synthesis pathway of the above reaction was as follows:

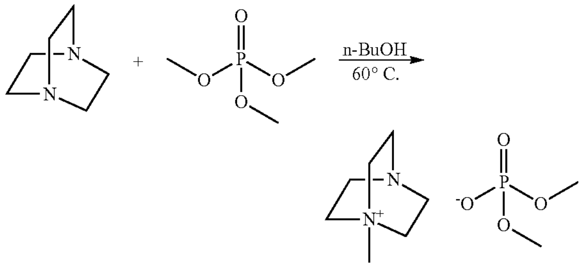

Ionic compound (1)

The measurement results of nuclear magnetic resonance spectrometry of Ionic compound (1) are shown below: $^1H$ NMR (400 MHz, ppm, $CD_3OD$): δ 3.50 (d, J=8.4 Hz, 6H), 3.354 (t, J=6.0 Hz, 6H), 3.20 (t, J=6.0 Hz, 6H), 3.04 (s, 3H).

Preparation of Ionic Compound (2)

Example 3

Trimethyl phosphate (0.22 mol) and 1,4-diazabicyclo [2.2.2]octane (0.10 mol) were added into a reaction bottle, and toluene (40 mL) (serving as solvent) was added into the reaction bottle. After heating at 100° C. for 12 hours, the reaction bottle was cooled to room temperature, and the obtained solid was collected. Next, the obtained solid was dissolved in water (50 mL), and water and toluene was removed with a rotary concentrator. Next, the result was subjected to a freeze drying process, obtaining Ionic compound (2) (with a structure of

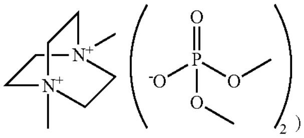

(white solid, with a yield of 92%). The synthesis pathway of the above reaction was as follows:

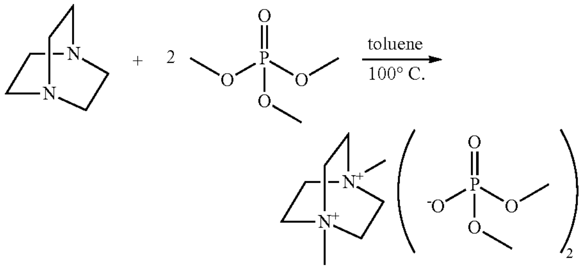

Ionic compound (2)

The measurement results of nuclear magnetic resonance spectrometry of are shown below: Ionic compound (2) $^{1}H$ NMR (400 MHz, ppm, $CD_3OD$): δ 4.02 (s, 12H), 3.58 (s, 6H), 3.56 (s, 6H), 3.36 (s, 6H).

Example 4

Trimethyl phosphate (0.44 mol) and 1,4-diazabicyclo[2.2.2]octane (0.2 mol) were added into a reaction bottle, and 1-butanol (n-BuOH) (50 mL) (serving as solvent) was added into the reaction bottle. After heating at 60° C. for 12 hours, the reaction bottle was cooled to room temperature. Next, and 1-butanol was removed with a rotary concentrator. Next, after baking the result was disposed in a vacuum oven at 110° C. for 12 hours, obtaining Ionic compound (2) (white solid, with a yield of 98%). The synthesis pathway of the above reaction was as follows:

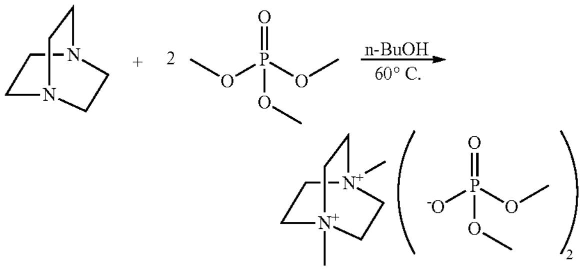

Ionic compound (2)

The measurement results of nuclear magnetic resonance spectrometry of Ionic compound (2) are shown below: $^{1}H$ NMR (400 MHz, ppm, $CD_3OD$): δ 4.02 (s, 12H), 3.58 (s, 6H), 3.56 (s, 6H), 3.36 (s, 6H).

Preparation of Ionic Compound (3)

Example 5

Triethyl phosphate (0.2 mol) and 1,4-diazabicyclo[2.2.2]octane (0.2 mol) were added into a reaction bottle, toluene (60 mL) (serving as solvent) was added into the reaction bottle. After heating at 100° C. for 12 hours, the reaction bottle was cooled to room temperature, and the lower-layer liquid was collected. Next, the obtained lower-layer liquid was dissolved in water (100 mL). After extracting three times using diethyl ether (60 mL), water phase was collected and an activated carbon (1 g) was added. After heating at 50° C. for 4 hours, the result was filtered. Next, the filtrate was concentrated, dehydrated and subjected to a freeze drying process, obtaining Ionic compound (3) (with a structure of

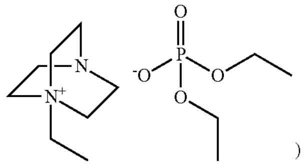

(light yellow liquid, with a yield of 93%). The synthesis pathway of the above reaction was as follows:

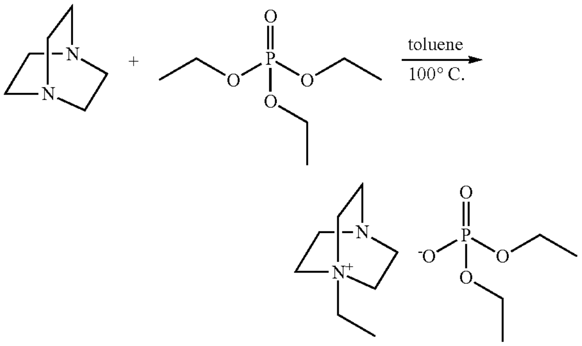

Ionic compound (3)

The measurement results of nuclear magnetic resonance spectrometry of Ionic compound (3) are shown below: $^{1}H$ NMR (400 MHz, ppm, $CD_3OD$): δ 3.94-3.82 (m, 4H), 3.31-3.27 (m, 8H), 3.18-3.14 (m, 6H), 1.32 (t, J=5.6 Hz, 3H), 1.21 (t, J=5.6 Hz, 6H).

Example 6

Triethyl phosphate (0.42 mol) and 1,4-diazabicyclo[2.2.2]octane (0.4 mol) were added into a reaction bottle, and 1-butanol (n-BuOH) (40 mL) (serving as solvent) was added into the reaction bottle. After heating at 100° C. for 12 hours, the reaction bottle was cooled to room temperature. Next, after extracting three times using ethyl acetate (50 mL), the lower-layer liquid was collected and the solvent was removed with a rotary concentrator. Next, after baking the result was disposed in a vacuum oven at 110° C. for 12 hours, obtaining Ionic compound (3) (light yellow liquid, with a yield of 92%). The synthesis pathway of the above reaction was as follows:

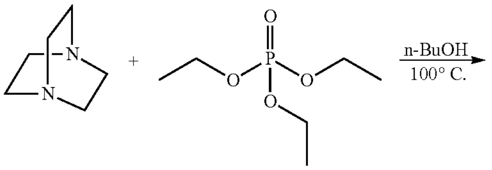

-continued

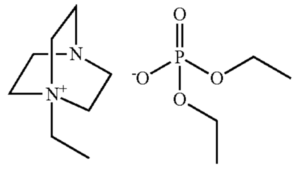

Ionic compound (3)

The measurement results of nuclear magnetic resonance spectrometry of Ionic compound (3) are shown below: $^1$H NMR (400 MHz, ppm, $CD_3OD$): δ 3.94-3.82 (m, 4H), 3.31-3.27 (m, 8H), 3.18-3.14 (m, 6H), 1.32 (t, J=5.6 Hz, 3H), 1.21 (t, J=5.6 Hz, 6H).

Preparation of Ionic Compound (4)

Example 7

Triethyl phosphate (0.25 mol) and 1,4-diazabicyclo[2.2.2]octane (0.1 mol) were added into a reaction bottle, and toluene (40 mL) (serving as solvent) was added into the reaction bottle. After heating at 100° C. for 12 hours, the reaction bottle was cooled to room temperature, the lower-layer liquid was collected. Next, the lower-layer liquid was dissolved in water (80 mL). After extracting three times using diethyl ether (50 mL), water phase was collected and an activated carbon (1 g) was added. After heating at 50° C. for 4 hours, the result was filtered. Next, the filtrate was concentrated, dehydrated and subjected to a freeze drying process, obtaining Ionic compound (4) (with a structure of

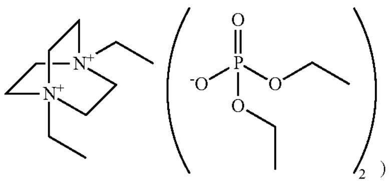

)

(light yellow liquid, with a yield of 90%). The synthesis pathway of the above reaction was as follows:

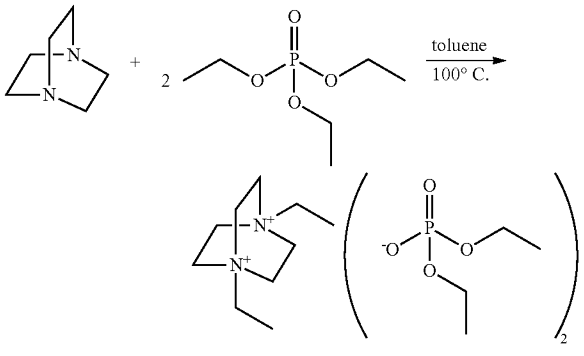

Ionic compound (4)

The measurement results of nuclear magnetic resonance spectrometry of Ionic compound (4) are shown below: $^1$H NMR (400 MHz, ppm, $CD_3OD$): δ 3.95 (s, 12H), 3.88 (quint, J=5.6 Hz, 8H), 3.64 (q, J=5.6 Hz, 4H), 1.43 (t, J=5.6 Hz, 6H), 1.23 (t, J=5.6 Hz, 12H).

Example 8

Triethyl phosphate (0.25 mol) and 1,4-diazabicyclo[2.2.2]octane (0.1 mol) were added into a reaction bottle, and 1-butanol (n-BuOH) (20 mL) (serving as solvent) was added into the reaction bottle. After heating at 140° C. for 12 hours, the reaction bottle was cooled to room temperature. Next, after extracting three times using ethyl acetate (40 mL), the lower-layer liquid was collected and the solvent was removed with a rotary concentrator. Next, after baking the result was disposed in a vacuum oven at 110° C. for 12 hours, obtaining Ionic compound (4) (light yellow liquid, with a yield of 92%). The synthesis pathway of the above reaction was as follows:

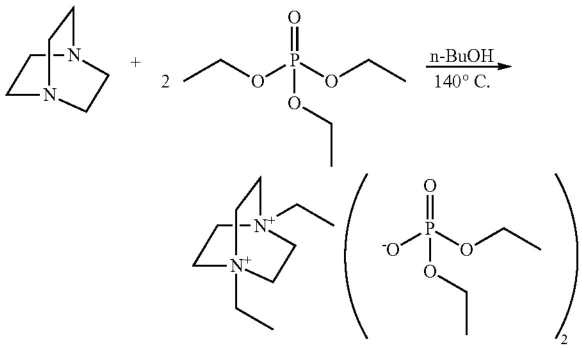

Ionic compound (4)

The measurement results of nuclear magnetic resonance spectrometry of Ionic compound (4) are shown below: $^1$H NMR (400 MHz, ppm, $CD_3OD$): δ 3.95 (s, 12H), 3.88 (quint, J=5.6 Hz, 8H), 3.64 (q, J=5.6 Hz, 4H), 1.43 (t, J=5.6 Hz, 6H), 1.23 (t, J=5.6 Hz, 12H).

Comparative Example 1

Triethyl phosphate (0.3 mol) and 1-methylimidazole (0.3 mol) were added into a reaction bottle. After heating at 140° C. for 12 hours, the reaction bottle was cooled to room temperature, the result was dissolved in water (80 mL). After extracting three times using diethyl ether (50 mL), water phase was collected and an activated carbon (1 g) was added. After heating at 50° C. for 4 hours, the result was filtered. Next, the filtrate was concentrated, dehydrated and subjected to a freeze drying process, obtaining Ionic compound (5) (with a structure of

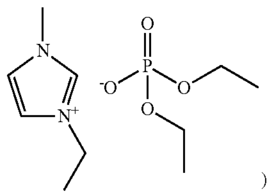

)

(light yellow liquid, with a yield of 90%). The synthesis pathway of the above reaction was as follows:

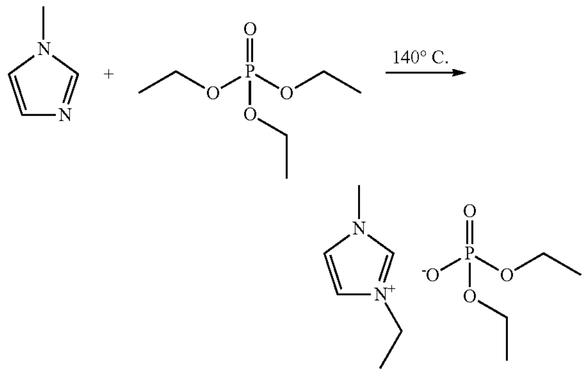

Ionic compound (5)

The measurement results of nuclear magnetic resonance spectrometry of Ionic compound (5) are shown below: $^1H$ NMR (400 MHz, ppm, $CD_3OD$): δ 8.95 (s, 1H), 7.66 (s, 1H), 7.59(s, 1H), 4.27 (q, J=6.0 Hz, 2H), 3.94 (s, 3H), 3.91 (quint, J=5.6 Hz, 4H), 1.55 (t, J=6.0 Hz, 3H), 2.26 (t, J=5.6 Hz, 6H).

Comparative Example 2

2-(N,N-dimethylamino)ethanol (DMAE) (0.1 mol) was added into a reaction bottle. Next, Trimethyl phosphate (0.1 mol) was dropwisely added into the reaction bottle. After heating at 55° C. for 24 hours, the reaction bottle was cooled to room temperature, obtaining a white solid. The solid was dissolved in water (50 mL). After extracting three times using diethyl ether (30 mL), water phase was collected. After dehydrating with a rotary concentrator, the result was disposed in vacuum oven at 60° C. for 12 hours, obtaining Ionic compound (6) (with a structure of

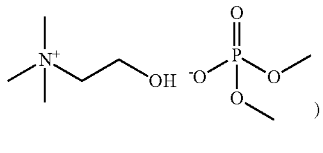
)

(light yellow liquid, with a yield of 92%). The synthesis pathway of the above reaction was as follows:

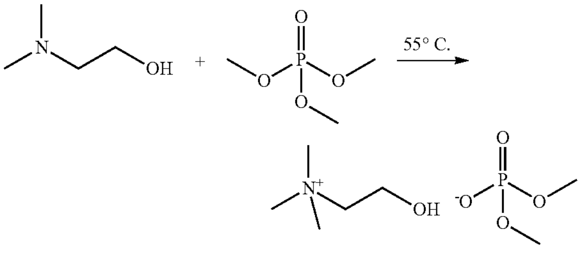

Ionic compound (6)

The measurement results of nuclear magnetic resonance spectrometry of Ionic compound (6) are shown below: $^1H$ NMR (400 MHz, ppm, $CD_3OD$): δ 3.99-3.96 (m, 2H), 3.55 (s, 3H), 3.53 (s, 3H), 3.48-3.46 (m, 2H), 3.20 (s, 9H).

Preparation of Absorbent

Example 9

Ionic compound (1) and water were mixed, wherein the weight ratio of Ionic compound (1) to water is 4:1. After stirring evenly, Absorbent (1) was obtained.

Examples 10-12

Examples 10-12 were performed in the same manner as in Example 9, except that Ionic compound (1) was replaced with Ionic compounds (2)-(4) respectively, obtaining Absorbents (2)-(4).

Comparative Examples 3 and 4

Comparative Examples 3 and 4 were performed in the same manner as in Example 9, except that Ionic compound (1) was replaced with Ionic compound (5) and (6) respectively, obtaining Absorbents (5) and (6).

Comparative Example 5

Ionic compound (7) (with a structure of

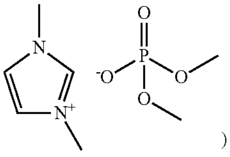
)

was provided. Ionic compound (7) and water were mixed, wherein the weight ratio of Ionic compound (7) to water is 4:1. After stirring evenly, Absorbent (7) was obtained.

Comparative Example 6

Ionic compound (8) (with a structure of

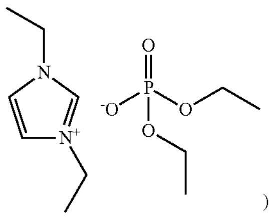
)

was provided. Ionic compound (8) and water were mixed, wherein the weight ratio of Ionic compound (8) to water is 4:1. After stirring evenly, Absorbent (8) was obtained.

Comparative Example 7

Ionic compound (9) (with a structure of

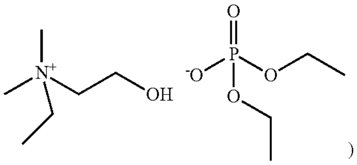

)

was provided. Ionic compound (9) and water were mixed, wherein Ionic compound (9) to water is 4:1. After stirring evenly, Absorbent (9) was obtained.

Comparative Example 8

Chlorinated lithium (LiCl) was provided. Chlorinated lithium and water were mixed, wherein the weight ratio of chlorinated lithium to water is 1:2. After stirring evenly, Absorbent (10) was obtained.

Measurement of Water Vapor Pressure

The water vapor pressure of Absorbents (1)-(4) were measured at 5° C., 10° C., 15° C., 20° C., 25° C., 30° C., 35° C., 40° C., 45° C., 50° C., 55° C., and 60° C., and the vapor pressure difference of Absorbents (1)-(4) at various temperature were determined, and the results are shown in Table 1. In addition, the water vapor pressure of Absorbents (5)-(10) were measured at 5° C., 10° C., 15° C., 20° C., 25° C., 30° C., 35° C., 40° C., 45° C., 50° C., 55° C., and 60° C., and the vapor pressure difference of Absorbents (5)-(10) at various temperature were determined, and the results are shown in Table 2.

The measurement method for the vapor pressure of the absorbent utilizes the melting-point model (reference: J. Chem. Eng. Data 2004, 49, 1550-1553) and includes following steps. Absorbent was disposed in a container, and the temperature was cooled to 5° C. After applying a vacuum until the evaporation of water vapor begins, the vacuum system was closed and the container was heated. The vapor pressure was measured using a pressure gauge (EJX310A, YOKOGAWA) at every 5° C.

TABLE 1

| | | Absorbent (1) | Absorbent (2) | Absorbent (3) | Absorbent (4) |
|---|---|---|---|---|---|
| ionic compound | | Ionic compound (1) | Ionic compound (2) | Ionic compound (3) | Ionic compound (4) |
| vapor pressure (kPa) | 5° C. | 0.29 | 0.36 | 0.29 | 0.57 |
| | 10° C. | 0.49 | 0.59 | 0.43 | 0.79 |
| | 15° C. | 0.76 | 0.87 | 0.65 | 1.09 |
| | 20° C. | 1.03 | 1.13 | 0.93 | 1.44 |
| | 25° C. | 1.32 | 1.44 | 1.27 | 1.85 |
| | 30° C. | 1.68 | 1.81 | 1.69 | 2.31 |
| | 35° C. | 2.11 | 2.25 | 2.21 | 2.89 |
| | 40° C. | 2.6 | 2.77 | 2.85 | 3.61 |
| | 45° C. | 3.21 | 3.43 | 3.61 | 4.48 |
| | 50° C. | 3.99 | 4.21 | 4.61 | 5.4 |
| | 55° C. | 4.97 | 5.16 | 5.77 | 6.68 |
| | 60° C. | 6.09 | 6.28 | 7.17 | 8.32 |
| vapor pressure difference (50° C. and 15° C.) (kPa) | | 3.23 | 3.34 | 3.96 | 4.31 |
| vapor pressure difference (60° C. and 15° C.) (kPa) | | 5.33 | 5.41 | 6.52 | 7.23 |

TABLE 2

| | | Absorbent (5) | Absorbent (6) | Absorbent (7) | Absorbent (8) | Absorbent (9) | Absorbent (10) |
|---|---|---|---|---|---|---|---|
| ionic compound | | Ionic compound (5) | Ionic compound (6) | Ionic compound (7) | Ionic compound (8) | Ionic compound (9) | LiCl |
| vapor pressure (kPa) | 5° C. | 0.47 | 0.29 | 0.39 | 0.41 | 0.56 | 0.29 |
| | 10° C. | 0.69 | 0.47 | 0.63 | 0.60 | 0.83 | 0.43 |
| | 15° C. | 0.95 | 0.68 | 0.91 | 0.88 | 1.16 | 0.65 |
| | 20° C. | 1.24 | 0.92 | 1.25 | 1.16 | 1.52 | 0.89 |
| | 25° C. | 1.59 | 1.21 | 1.67 | 1.49 | 1.92 | 1.19 |
| | 30° C. | 2.01 | 1.56 | 2.11 | 1.92 | 2.44 | 1.55 |
| | 35° C. | 2.51 | 1.99 | 2.64 | 2.43 | 3.07 | 2.00 |
| | 40° C. | 3.12 | 2.51 | 3.27 | 3.07 | 3.79 | 2.51 |
| | 45° C. | 3.87 | 3.15 | 4.04 | 3.83 | 4.61 | 3.15 |
| | 50° C. | 4.79 | 3.95 | 4.95 | 4.77 | 5.56 | 3.95 |
| | 55° C. | 5.91 | 4.96 | 5.97 | 5.96 | 6.91 | 4.95 |
| | 60° C. | 7.33 | 6.08 | 7.63 | 7.76 | 8.57 | 6.01 |
| vapor pressure difference (50° C. and 15° C.) ($Vp_{50-15}$) (kPa) | | 3.84 | 3.27 | 4.04 | 3.89 | 4.4 | 3.3 |
| vapor pressure difference (60° C. and 15° C.) ($Vp_{60-15}$) (kPa) | | 6.38 | 5.4 | 6.72 | 6.88 | 7.41 | 5.36 |

The measured water vapor pressure of the Absorbent (10) of the disclosure (chlorinated lithium aqueous solution) is consistent with the values reported in the related literature (Applied Thermal Engineering 2017, 124, 271-278).

The dehumidification capability of the absorbent can be evaluated via its water vapor pressure. When the absorbent is operating in an absorption device, it absorbs water vapor from the surrounding environment to reduce the humidity, driven by the difference between the water vapor pressure in the air and the saturated vapor pressure on the absorbent surface. The lowest relative humidity for dehumidifying air via the absorbent can be evaluated based on the water vapor pressure of the absorbent. A lower water vapor pressure of the absorbent indicates a stronger water-vapor absorption capacity of the absorbent (i.e., ionic compound aqueous solution) at the specific temperature.

As shown in Table 1, it was observed that the absorbent prepared from the ionic compound of the disclosure has a water vapor pressure less than or equal to 1.1 kPa at 5-20° C.

In addition, a lower water vapor pressure indicates a stronger affinity for water (less tendency to desorb water), and water vapor pressure increases with temperature. Therefore, when the absorbent exhibits a larger vapor pressure difference within a specific temperatures range, it means that a greater capacity to absorb and desorb water within the specific temperatures range (i.e., a higher dehumidification capacity). Consequently, when the absorbent shows a larger vapor pressure difference within a specific temperatures range, the absorbent exhibits higher dehumidification efficiency (i.e., the absorbent exhibits higher dehumidification capability).

As shown in Table 2, chlorinated lithium aqueous solution exhibits low water vapor pressure at low temperatures (i.e. good water affinity), but the vapor pressure difference ($Vp_{60-15}$) is low. It means that chlorinated lithium aqueous solution retains water vapor even at 60° C. and requires further heating to higher temperatures for effective desorption, thereby increasing energy consumption for absorbent regeneration.

As shown in Tables 1 and 2, the absorbents prepared from the ionic compounds of the disclosure (i.e. Absorbents (1)-(4)) exhibit larger vapor pressure differences ($Vp_{50-15}$) between 15° C. and 50° C., as well as between 15° C. and 60° C. ($Vp_{60-15}$), in comparison with the chlorinated lithium aqueous solution (absorbent (10)). Therefore, the ionic compound of the disclosure has the potential to reduce the energy consumption required for absorbent regeneration and improve the dehumidification efficiency of the absorbent.

Corrosion Test

Copper foils (C1100P) (with a size of 10×10×2 $mm^3$) were provided and weighed. Next, Copper foils were disposed in sample vials with various absorbents (i.e. Absorbents (1)-(10)) (8 mL) and tap water respectively. After stifling at 80° C. for 2 days, the copper foils was isolated, dried and weighed, and the percentage change in weight of copper foil was determined and the results are shown in Table 3. Next, the copper foils was replaced with aluminum foils (A5052) (with a size of 10×10×2 $mm^3$) and stainless steel foils (SUS304) (with a size of 10×10×2 $mm^3$) and the above steps were repeated. The results are shown in Table 3.

TABLE 3

| | percentage change in weight (%) | | |
|---|---|---|---|
| | stainless steel foil | aluminum foil | copper foil |
| Absorbent (1) | ±0.0000% | ±0.0000% | −0.0119% |
| Absorbent (2) | ±0.0000% | ±0.0000% | −0.0120% |
| Absorbent (3) | ±0.0000% | ±0.0000% | −0.0239% |
| Absorbent (4) | ±0.0000% | ±0.0000% | −0.0695% |
| Absorbent (5) | +0.0336% | +0.1389% | −0.4935% |

TABLE 3-continued

| | percentage change in weight (%) | | |
|---|---|---|---|
| | stainless steel foil | aluminum foil | copper foil |
| Absorbent (6) | +0.0336% | ±0.0000% | −0.0638% |
| Absorbent (7) | +0.0408% | +0.2041% | −0.1957% |
| Absorbent (8) | −0.0202% | +0.1572% | −0.7364% |
| Absorbent (9) | −0.0134% | +0.0999% | −0.1164% |
| Absorbent (10) | −0.0136% | −0.1255% | −0.0524% |
| tap water | ±0.0000% | +0.0827% | +0.0299% |

As shown in Table 3, chlorinated lithium and Absorbents (5)-(10) exhibit various degrees of corrosiveness regarding to stainless steel foils, aluminum foils, and copper foils. Furthermore, according to Table 3, the absorbents prepared from the ionic compound of the disclosure (Absorbents (1)-(4)) demonstrate minimal corrosion regarding to stainless steel foils and aluminum foils, and also exhibit lower corrosion regarding to copper foils.

Viscosity Measurement

The viscosities of Absorbents (1)-(4) at various temperatures were measured by a viscosity meter (DV-II+Pro, Brookfield), and the results are shown in Table 4.

TABLE 4

| | | Absorbent (1) | Absorbent (2) | Absorbent (3) | Absorbent (4) |
|---|---|---|---|---|---|
| viscosity (cP) | 15° C. | 214 | 184 | 134 | 55 |
| | 20° C. | 149 | 135 | 94 | 41 |
| | 25° C. | 104 | 99 | 68 | 32 |
| | 30° C. | 74 | 66 | 50 | 26 |
| | 35° C. | 54 | 54 | 38 | 21 |
| | 40° C. | 41 | 42 | 30 | 17 |
| | 45° C. | 31 | 33 | 24 | 14 |
| | 50° C. | 26 | 28 | 20 | 12 |

Viscosity is also an important parameter for evaluating absorbents. When the viscosity of an absorbent is too low, it becomes prone to liquid carryover, where liquid is entrained and carried out with the air, resulting in environmental pollution. On the other hand, when the viscosity of an absorbent is too high, it reduces the flowability of the absorbent, increasing the energy consumption of the pump. As shown in Table 4, the absorbents prepared from the ionic compounds of the disclosure, possess the viscosity of 50 cP to 220 cP at 15° C., suitable for applications in dehumidification systems that adopt spray or liquid flow processes.

Odor and Degradation Evaluation

As the air introduced by the dehumidification system comes into direct contact with the absorbent, if an ionic compound produces odors, it may be less suitable for use in air condition systems. Absorbents (1)-(4) prepared from the ionic compound of the disclosure were stored at room temperature and atmospheric pressure for 180 days. Following the evaluation, Absorbents (1)-(4) did not undergo degradation and did not exhibit any noticeable odor generation.

Accordingly, the absorbent including the ionic compound of the disclosure exhibits a higher water-vapor absorption capacity and a lower desorption temperature thereby increasing the dehumidification efficiency of the absorption device that utilizes the absorbent. Additionally, the liquid absorbent containing the ionic compound of the disclosure offers advantages such as odorless, antibacterial, low corrosiveness, fluidity, and excellent room temperature stability, which can be widely applied to various dehumidification devices.

It will be clear that various modifications and variations can be made to the disclosed methods and materials. It is intended that the specification and examples be considered as exemplary only, with the true scope of the disclosure being indicated by the following claims and their equivalents.

What is claimed is:

1. An ionic compound, having a structure represented by Formula (I):

$AB_n$ Formula (I)

wherein, A is

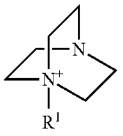
or
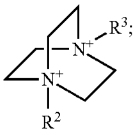

B is

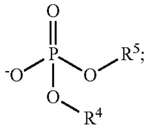

$R^1$, $R^2$, $R^3$, $R^4$, and $R^5$ are independently $C_{1-6}$ alkyl group; and n is 1 or 2.

2. The ionic compound as claimed in claim 1, wherein $R^1$, $R^2$, $R^3$, $R^4$, and $R^5$ are independently methyl, ethyl, n-propyl, isopropyl, n-butyl, sec-butyl, iso-butyl, tert-butyl, pentyl or hexyl.

3. The ionic compound as claimed in claim 1, wherein A is

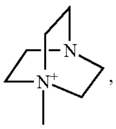,
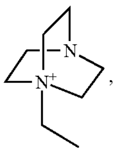,
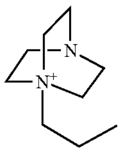,
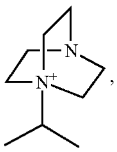,
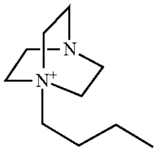,
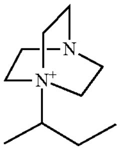,
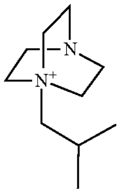,
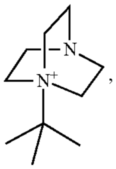,
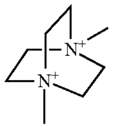,
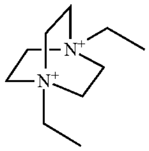, -continued

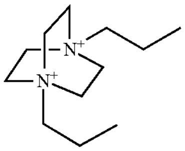,
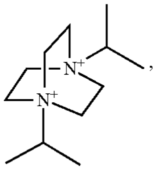,
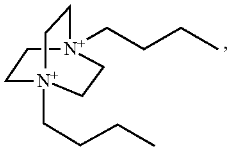,
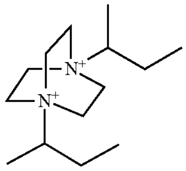,
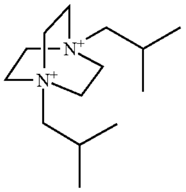, or
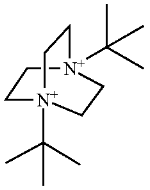.

4. The ionic compound as claimed in claim 1, wherein B is

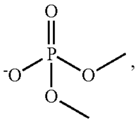,
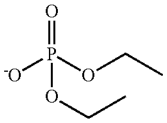,
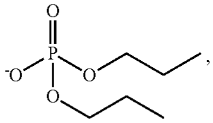,
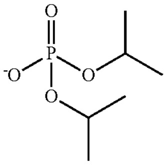,
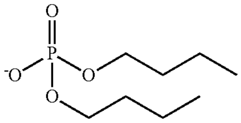,
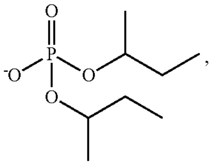,
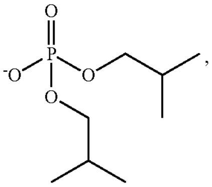,
or
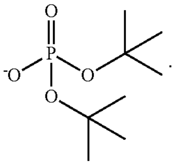.

5. The ionic compound as claimed in claim 1, wherein A is

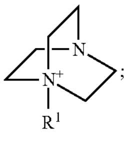;

B is

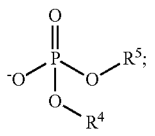

n is 1; and $R^1$, $R^4$, and $R^5$ are independently $C_{1-6}$ alkyl group.

6. The ionic compound as claimed in claim 1, wherein A is

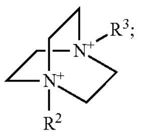

B is

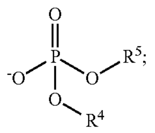

n is 2; and $R^2$, $R^3$, $R^4$, and $R^5$ are independently $C_{1-6}$ alkyl group.

7. An absorbent, comprising:

an ionic compound, wherein the ionic compound has a structure represented by Formula (I)

$AB_n$ Formula (I)

wherein, A is

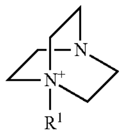

or

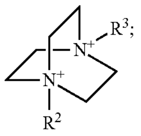

B is

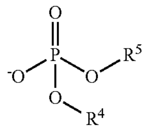

or

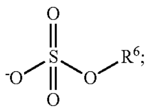

$R^1$, $R^2$, $R^3$, $R^4$, $R^5$, and $R^6$ are independently H, $C_{1-6}$ alkyl group; and n is 1 or 2; and a solvent, wherein the weight ratio of the ionic compound to the solvent is 1:9 to 9:1.

8. The absorbent as claimed in claim 7, wherein the solvent is water, methanol, ethanol, propanol, butanol, ammonia, or a combination thereof.

9. The absorbent as claimed in claim 7, wherein the solvent is water, and the weight ratio of the ionic compound to the water is 4:1, wherein the absorbent has a viscosity of 50 cP to 220 cP at 15° C.

10. An absorption device, comprising:

a chamber; and an absorbent disposed in the chamber, wherein the absorbent is the absorbent as claimed in claim 7.

* * * * *